(12) United States Patent
Park et al.

(10) Patent No.: US 9,163,272 B2
(45) Date of Patent: Oct. 20, 2015

(54) PROTEIN SYNTHESIS KIT, AND METHOD FOR EXPRESSING AND EXTRACTING PROTEINS USING AUTOMATIC EXTRACTION EQUIPMENT

(75) Inventors: Han Oh Park, Daejeon (KR); You Sang Cho, Daejeon (KR); Jun Ho Jung, Seoul (KR); Ji Won Han, Daejeon (KR); Nam Il Kim, Daejeon (KR)

(73) Assignee: BIONEER CORPORATION, Daejeon (KR)

(*) Notice: Subject to any disclaimer, the term of this patent is extended or adjusted under 35 U.S.C. 154(b) by 0 days.

(21) Appl. No.: 14/238,908

(22) PCT Filed: Aug. 23, 2012

(86) PCT No.: PCT/KR2012/006715
§ 371 (c)(1),
(2), (4) Date: Feb. 14, 2014

(87) PCT Pub. No.: WO2013/032174
PCT Pub. Date: Mar. 7, 2013

(65) Prior Publication Data
US 2014/0212919 A1 Jul. 31, 2014

(30) Foreign Application Priority Data

Aug. 26, 2011 (KR) .................. 10-2011-0085824
Aug. 17, 2012 (KR) .................. 10-2012-0090149

(51) Int. Cl.
C07K 1/22 (2006.01)
C07K 1/00 (2006.01)
C07K 1/14 (2006.01)
C12P 21/00 (2006.01)
B01J 19/00 (2006.01)
C12P 21/02 (2006.01)

(52) U.S. Cl.
CPC .............. *C12P 21/00* (2013.01); *B01J 19/0046* (2013.01); *C07K 1/22* (2013.01); *C12P 21/02* (2013.01); *B01J 2219/00315* (2013.01); *B01J 2219/00364* (2013.01); *B01J 2219/00459* (2013.01); *B01J 2219/00495* (2013.01)

(58) Field of Classification Search
CPC .............. C07K 1/00; C07K 1/14; C07K 1/22
See application file for complete search history.

(56) References Cited

U.S. PATENT DOCUMENTS 6,927,025 B1* 8/2005 Carr et al. .................... 435/6.14
2006/0211083 A1* 9/2006 Katzen et al. ................ 435/68.1
2007/0259374 A1* 11/2007 Griffiths et al. .................. 435/6
2011/0009608 A1* 1/2011 Kim et al. .................. 536/25.41
2012/0316078 A1* 12/2012 Sykes et al. ....................... 506/9

FOREIGN PATENT DOCUMENTS

| CN | 101363045 A | 2/2009 |
|---|---|---|
| EP | 1411131 A1 | 4/2004 |
| EP | 1619247 A1 | 1/2006 |
| EP | 2565260 A2 | 3/2013 |
| JP | 7-31494 A | 2/1995 |
| JP | 2003-9877 A | 1/2003 |
| JP | 2006042601 A2 | 2/2006 |
| JP | 2011516075 A | 5/2011 |
| KR | 10-1025135 B1 | 3/2011 |
| WO | 2006078821 A2 | 7/2006 |
| WO | 2008/010687 A1 | 1/2008 |

OTHER PUBLICATIONS

Kim et al., 2006, Cell-free synthesis and in situ isolation of recombinant proteins, Protein Expression and Purification, 45: 249-254.*
Gan et al., 2008, Microbeads Display of Proteins Using Emulsion PCR and Cell-Free Protein Synthesis, Biotechnol. Prog., 24: 1107-1114.*
Lee et al., "Ribosomal synthesis and in situ isolation of peptide molecule in a cell-free translation system", Protein Expression and Purification, 2010, vol. 71, pp. 16-20.
European Patent Office, Communication dated Mar. 2, 2015, issued in corresponding European Application No. 12828394.2.
Hoffman et al., "Rapid translation system: A novel cell-free way from gene to protein", Biotechnology Annual Review, 2004, vol. 10, pp. 1-30.
Yabuki et al., "A robust two-step PCR method of template DNA production for high-throughput cell-free protein synthesis", J Struct Funct Genomics, 2007, vol. 8, pp. 173-191.
The State Intellectual Property Office of the People's Republic of China, Communication dated Apr. 1, 2015, issued in corresponding Chinese Application No. 201280041689.1.
Japan Patent Office, Communication dated Apr. 28, 2015, issued in corresponding Japanese Application No. 2014-527074.

* cited by examiner

*Primary Examiner* — Amber D Steele
(74) *Attorney, Agent, or Firm* — Sughrue Mion, PLLC

(57) ABSTRACT

Provided is a method of protein synthesis. The method of protein synthesis according to the present invention uses an automatic biological material purification apparatus including: a well plate kit; a heating part; and a magnetic field applying part, such that a plurality of target proteins may be more quickly and simply obtained as compared to target proteins obtained by using the existing method for expressing/purifying proteins through conventional cell culture, and a reproducible synthesis efficiency on the same proteins may be obtained due to no deviation between reaction wells.

11 Claims, 12 Drawing Sheets

Template - Plasmid DNA

M1; AccuLadder™ Protein Size Marker (Low)
 1; CalmL3 (17.5kDa), 2; RNase H (20kDa), 3; DUSP 3 (22kDa),
 4; CAT (24kDa), 5; AcGFP (29kDa), 6; EF-Ts (34kDa), 7; VF (45kDa),
 8; Poly A polymerase (50kDa), 9; MMLV RTase (75kDa), 10; BM3 (117kDa)
M2; AccuLadder™ Protein Size Marker (Broad)

Template - PCR product

M; AccuLadder™ Protein Size Marker (Low),
 1; SAV (13 kDa), 2; RNase H (20 kDa), 3; hGH (23 kDa),
 4; CAT (26.5 kDa), 5; UDG (28 kDa), 6; AcGFP (28 kDa),
 7; EVO (30 kDa), 8; RFP (31 kDa), 9; Poly A polymerase (54 kDa)

PROTEIN SYNTHESIS KIT, AND METHOD FOR EXPRESSING AND EXTRACTING PROTEINS USING AUTOMATIC EXTRACTION EQUIPMENT

CROSS REFERENCE TO RELATED APPLICATIONS

This application is a National Stage of International Application No. PCT/KR2012/006715 filed Aug. 23, 2012, claiming priority based on Korean Patent Application Nos. 10-2011-0085824 filed Aug. 26, 2011 and 10-2012-0090149 filed Aug. 17, 2012, the contents of all of which are incorporated herein by reference in their entirety.

TECHNICAL FIELD

The present invention relates to a method for producing proteins, and more particularly, to a method for producing proteins including simultaneously performing expression and purification of target proteins in an automatic system using an automatic biological material purification apparatus including: a heating part; and a magnetic field applying part.

BACKGROUND ART

As a method for expressing recombinant proteins, a method for mainly using cells such as *Escherichia coli* and yeast, transforming a recombinant protein expression vector into the cell, and culturing the transformed cells to express proteins has been generally used. The above-described method requires a strain selection process which stably expresses recombinant protein and has a difficulty in expressing protein having toxicity in a cell, such that it takes at least several days to months to obtain one protein.

Recently, a cell-free protein expression method synthesizing protein in a test tube without using cells has received attention, and various products related thereto has been developed. The cell-free protein expression method, which is a system of expressing protein by adding a template DNA capable of expressing protein, for example, an expression vector, a PCR product, a cell lysate, an expression solution, and a diethylpyrocarbonate (DEPC) distilled water into a tube, and performing a reaction at a proper temperature (30 to 40° C.) for a proper time (1 to 3 hours), has an advantage in that proteins having toxicity in a cell are capable of being expressed, and a required time may be remarkably reduced as compared to the above-mentioned method for expressing proteins using cells. Here, in order to express proteins, proper temperature and time are required. The reason is that an activity on an enzyme should be accompanied during all processes including synthesis of RNA from DNA in a tube and synthesis of protein from the RNA, wherein the above-described processes are capable of being performed in the case of maintaining a temperature when activities of a plurality of enzymes are shown, that is, 30 to 40° C.

Since a plurality of proteins are mixed in a sample having expressed recombinant proteins, in order to easily purify the recombinant protein expressed from the sample, the expressed proteins should have an affinity with a specific material. Recently, a method for purification proteins by expressing a coupled state between recombinant protein and histidine and using an affinity of histidine and metal ions (nickel ion, cobalt ion, and the like) has been mainly used, and various products related thereto have been on sale. Among the methods, a method for using magnetic particles has been mainly used, wherein metal ions on a surface of the magnetic particles are coupled with histidine of the target protein, such that the target protein only is capable of being extracted from a plurality of proteins.

However, according to the existing technologies according to the related art, high yield and high-purity purification may not be achieved and it is difficult to control protein complicated expression due to cell culture, which is non-effective, such that a basic issue which is reproducible production on the same proteins still has not been overcome.

Therefore, a method for producing proteins capable of achieving high yield and high-purity purification and having reproducible synthesis efficiency on the same protein is required.

Technical Problem

The present inventors found a method for synthesis proteins including simultaneously performing expression and extraction of target proteins to be more effectively and easily performed as compared to the related art in a continuous study of an expression system effectively and easily controlling an expression of proteins and a method for biosynthesizing proteins using the same, thereby completing the present invention.

An object of the present invention is to provide a method for synthesis proteins including simultaneously performing expression and extraction of target proteins in an automatic system using an automatic biological material purification apparatus including: a heating part; and a magnetic field applying part.

In addition, an object of the present invention is to provide a protein synthesis kit simultaneously performing expression and purification of target proteins by combining a method for expressing cell-free protein with a method for purification protein using magnetic particles coupled with an affinity tag.

Technical Solution

In order to achieve objects of the present invention, there is provided a method for producing proteins capable of synthesizing and producing up to 16 kinds of target proteins within 6 hours using an automatic biological material purification apparatus including: a heating part; and a magnetic field applying part and applied by a combination of a method for expressing a cell-free protein with a method for purification proteins using magnetic particles coupled with an affinity tag.

Hereinafter, the present invention will be described in detail.

In one general aspect, a method for producing proteins includes:

(1) preparing a template for cell-free protein synthesis;

(2) adding the template to a cell-free protein expression solution to express proteins;

(3) adding magnetic particles coupled with an affinity tag to the expressed protein to attach a target protein to the magnetic particles; and (4) separating the attached target protein from the magnetic particles, wherein expression and purification of the target protein are simultaneously performed in an automatic system using an automatic biological material purification apparatus including: a heating part; and a magnetic field applying part.

A second multi well plate kit 420' and a first multi well plate kit 420 may be used, the second multi well plate kit 420' including:

(a) a solution for diluting the template for cell-free protein synthesis;

(b) the cell-free protein expression solution for expressing the target protein from the template; and the first multi well plate kit 420 including: (c) a magnetic particle solution for attaching the target protein to the magnetic particles;

(d) an eluting solution for the target protein;

(e) a magnetic particle reaction solution for coupling the target protein with the magnetic particle and a washing solution.

In another general aspect, a method for producing proteins includes:

(1) preparing a template for cell-free protein synthesis;

(2) adding the template to a cell-free protein expression solution to express proteins;

(3) adding magnetic particles coupled with an affinity tag to the expressed protein to attach a target protein to the magnetic particles; and (4) separating the attached target protein from the magnetic particles, wherein an automatic biological material purification apparatus including: a heating part; and a magnetic field applying part is used, a second multi well plate kit 420' and a first multi well plate kit 420 are used, the second multi well plate kit including: (a) a solution for diluting the template for cell-free protein synthesis; (b) the cell-free protein expression solution for expressing the target protein from the template; and the first multi well plate kit including: (c) a magnetic particle solution for attaching the target protein; (d) an eluting solution for the target protein; (e) a magnetic particle reaction solution for coupling the target protein with the magnetic particle and a washing solution, and expression and purification of the target protein are simultaneously performed in an automatic system.

The template for cell-free protein synthesis may be deoxyribonucleic acid (DNA) having a circular form or a linear form. Preferably, a plasmid DNA may be used as the DNA having a circular form, a PCR product may be used as the DNA having a linear form, but the present invention is not limited thereto.

In detail, the DNA having a linear form may be produced by obtaining a primary reactant by amplifying a target gene in a sample using a prepared primer set so as to amplify the target gene and provide overlapping sequences at 5' and 3' terminals and a premix for PCR; and secondarily amplifying the obtained primary reactant using the premix for PCR (hereinafter, referred to as 'a kit for PCR') containing the following composition A,

[Composition A]

(a) an upstream cassette set and a downstream cassette set positioned at both 5' and 3' terminals of the target gene, and (b) a secondary primer set having overlapping sequences at both 5' and 3' terminals of the cassette set.

The premix for PCR, which is a mixture containing mixed components required for an amplification reaction, may contain deoxynucleotide triphosphate mixture (dNTP mixture) and a buffer, and thermostable DNA polymerase such as Taq DNA polymerase. In addition, the premix for PCR may be prepared in a liquid or dried form.

In the present invention, a kit for PCR used in producing DNA having a linear form may contain a premix for PCR, 0.1 to 0.5 ng/ul of cassette set for encoding an affinity tag at both 5' and 3' terminals of a target gene and 0.1 to 1.0 pmoles/ul of each of secondary forward and reverse primers having overlapping sequences at 5' and 3' terminals of the cassette set.

In the present invention, a term: 'cassette' is collectively referred to as oligonucleotide having double strand which is shortly synthesized so as to be artificially connected to DNA product. Since a phosphate group is not found at 5' terminal of the cassette, a single strand only in cassette consisting of double strands may be connected to a genome DNA.

In the present invention, a term: 'primer', which is a singe strand nucleic acid sequence having a short and free 3' hydroxyl group, indicates a short nucleic acid sequence forming a template and a base pair of a complementary nucleic acid and functioning as a starting point for a strand copy of an nucleic acid template. The primer may initiate DNA synthesis in the presence of and reagent for polymerization reaction (that is, DNA polymerase) and different four dNTPs under appropriate buffer and temperature. A kit for PCR of the present invention includes a specific primer to a nucleotide sequence of a target gene and a specific primer to a cassette sequence.

In the present invention, the automatic biological material purification apparatus including: a heating part; and a magnetic field applying part may include a pipette block 100 having a plurality of separable pipettes 141 and 142 mounted thereon and pipetting a biological sample containing a target material to each of the plurality of pipettes 141 and 142; a fixing body 200 supporting the pipette block 100; a pipette block up-and-down moving part mounted on the fixing body 200 and vertically moving the pipette block 100; a pipette block back-and-forth moving part horizontally moving the fixing body 200 to horizontally move the pipette block 100; a base plate 400 positioned in a lower portion of the fixing body 200 and mounted with multi well plate kits 420' and 420 having a plurality of unit wells configuring two column wells adjacent to each other; a magnetic field applying part 700 positioned in a lower portion of a specific unit well of the multi well plate kits 420' and 420 in order to apply a magnetic field to the specific unit well of the multi well plate kits 420' and 420 and remove the magnetic field therefrom; and heating part 810 heating the specific unit well of the multi well plate kits 420' and 420.

In addition, in the automatic biological material purification apparatus including: a heating part; and a magnetic field applying part according to the present invention, the magnetic mounting part having a magnet mounted thereon and a heating part for heating are vertically moved, such that temperature may be controlled while applying or removing a magnetic field, and well inserting grooves which are a plurality of columns formed in the magnet mounting part cover the lower portion of the unit well of the multi well plate kits, such that a reaction efficiency may be more increased.

In detail, the magnetic field applying part 700 may include a magnet mounting part 710 on which a magnet 711 is mounted; and a lifting part 760 lifting up and down the magnet mounting part 710; wherein the magnet mounting part 710 has unit well inserting grooves 713 formed thereon so as to insert the lower portion of the specific unit well of the multi well plate kits 420' and 420, and the base plate 400 has unit well exposing holes 400-3 so that at the time of lifting up the magnet mounting part 710, the lower portion of the specific unit well of the multi well plate kits 420' and 420 inserts the unit well inserting groove 713, the lower portion of the specific unit cell of the multi well plate kits 420' and 420 is spaced apart by a predetermined distance from the lower portion of the unit well of the multi well plate kits 420' and 420 adjacent thereto so as to insert the unit well inserting groove 713, and the magnet 711 is inserted and mounted around the unit well inserting groove 713.

The method may include: Injecting step S10 injecting the template for cell-free protein synthesis into a unit well of the multi well plate kit 420';

First mixing step S20 mixing a DEPC distilled water injected into the unit well of the multi well plate kit 420' in order to dilute the template with the injected template;

Second mixing step S30 mixing a cell-free protein expression solution with a mixture of the first mixing step;

Mixture preparing step S40 preparing a protein synthesis reaction solution by mixing the mixture of the second mixing step with a cell disrupted liquid;

Heating step S50 applying heat to the protein synthesis reaction solution in the specific unit well by heating a lower portion of the specific unit well of the multi well plate kit 420' having the mixture using a heating unit 720;

Preparing step S70 of a magnetic particle reaction mixture;

protein expression injecting step S110 injecting the protein expression injected into the unit well of the multi well plate kit 420' into the prepared magnetic particle reaction mixture;

Reacting step S120 reacting the protein expression injected into the unit well of the multi well plate kit 420' with the magnetic particle;

Removing step S140 removing a mixture except for the magnetic particles and proteins coupled with the magnetic particle by applying a magnetic field to the mixture containing the protein expression;

Washing step S150 washing impurities except for the target protein from the magnetic particle by injecting a washing solution injected into the unit well of the multi well plate kit 420;

Removing step S170 removing a mixture except for the magnetic particles having the target proteins attached thereto from a washing solution containing mixture containing the washing solution by applying a magnetic field to the mixture containing the washing solution containing mixture;

Target protein separating step S180 separating the target protein by injecting the eluting solution for the target protein injected into the unit well of the multi well plate kit 420 into a mixture obtained from the removing step; and Target protein containing solution obtaining step S200 obtaining the target protein containing solution except for the magnetic particles from the eluting solution for the target protein containing the target protein separated from the magnetic particles by applying a magnetic field to the mixture.

In detail, the injecting step S10, which injects the template for cell-free protein synthesis into a unit well L of the multi well plate kit 420' using the plurality of pipettes 141 and 142 mounted on the automatic biological material purification apparatus including the heating part and the magnetic field applying part, is performed and after the injecting step S10, a first mixing step S20 is performed.

The first mixing step S20, which mixes a DEPC distilled water H for diluting the template for the cell-free protein synthesis injected into the unit well of the multi well plate kit 420' with the template for the cell-free protein synthesis injected to the unit well L of the multi well plate kit 420' using the plurality of pipettes 141 and 142 mounted in the automatic biological material purification apparatus including the heating part and the magnetic field applying part, is performed and after the first mixing step S20, a second mixing step S30 is performed.

The second mixing step S30, which mixes a cell-free protein expression solution injected with the specific unit well G of the multi well plate kit 420' with the unit well L injected with the template for the cell-free protein synthesis mixed with the DEPC distilled water injected into the unit well of the multi well plate kit 420' using the pipettes 141 and 142, is performed and after the second mixing step S30, a mixture preparing step S40 is performed.

The mixture preparing step S40, which prepares a protein synthesis reaction solution by mixing a cell disrupted liquid injected into a cell disrupted liquid storage tube 442-1 with the unit well L injected with the template for the cell-free protein synthesis mixed with the DEPC distilled water injected into the unit well of the multi well plate kit 420' using the pipettes 141 and 142, is performed and after the mixture preparing step S40, a heating step S50 is performed.

The heating step S50, which is a first heating step applying heat to the protein synthesis reaction solution in the specific unit well L by heating a lower portion of the specific unit well L of the multi well plate kit 420' using the heating part 720 in a state in which the lower portion of the specific unit well L of the multi well plate kit 420' inserts a unit well inserting groove 713 by lifting up the magnet mounting part 710, is performed and after the heating step S50, a first protein expression injecting step S60 is performed.

The first protein expression injecting step S60, which injects the first protein expression reacted in the protein synthesis reaction solution in the specific unit well L into a unit well J of the multi well plate kit 420' using the pipettes 141 and 142, is performed and after the first protein expression injecting step S60, a preparing step S70 of a magnetic particle reaction mixture is performed.

The preparing step of the magnetic particle reaction mixture S70, which mixes the magnetic particle reaction solution injected into a unit well A of the multi well plate kit 420 with the magnetic particles injected into a unit well F of the multi well plate kit 420 using the pipettes 141 and 142, is performed and after the preparing step of the magnetic particle reaction mixture S70, an injecting step of the reaction solution mixed with the magnetic particle S80, a first magnetic field applying step S90, and a first removing step S100 may be further performed in sequence.

The injecting step of the reaction solution mixed with the magnetic particles S80, which is a second injecting step injecting the mixture mixed with the magnetic particle reaction solution into the specific unit well L of the multi well plate kit 420' using the pipettes 141 and 142 in a state in which the magnet mounting part 710 is lifted down, is performed, and after the second injecting step S80, the first magnetic field applying step S90 is performed.

The first magnetic field applying step S90, which applies a magnetic field to the lower portion of the specific unit well of the multi well plate kit 420' from the magnet mounting part 710 by lifting up the magnet mounting part 710 so as to insert the lower portion of the specific unit well L of the multi well plate kit 420' into the unit well inserting groove 713, is performed, and after the first magnetic field applying step S90, a first removing step S100 is performed.

The first removing step S100, which removes a mixture except for the magnetic particles and materials attached to the magnetic particle from the mixture mixed with the magnetic particle reaction solution using the pipettes 141 and 142 in a state in which the magnetic particles and the materials attached to the magnetic particle in the mixture mixed with the magnetic particle reaction solution are attached to an inner wall of the lower portion of the specific unit well of the multi well plate kit 420' by a magnetic field applied to the lower portion of the specific unit well L of the multi well plate kit 420', is performed, and after the first removing step S100, a protein expression injecting step S110 is performed.

The protein expression injecting step S110, which injects the first protein expression injected into the unit well J of the multi well plate kit 420' into the unit well L of the multi well plate kit 420' using the pipettes 141 and 142, is performed, and after the second protein expression injecting step S110, a reacting step S120 is performed.

The reacting step S120, which reacts the second protein expression injected into the unit well L of the multi well plate kit 420' with the magnetic particle injected into the unit well L of the multi well plate kit 420' using the pipettes 141 and 142, is performed, and after the reacting step S120, a second magnetic field applying step S130 may be further performed.

The further performed second magnetic field applying step S130, which applies a magnetic field to the lower portion of the specific unit well L of the multi well plate kit 420' from the magnet mounting part 710 by lifting up the magnet mounting part 710 so as to insert the lower portion of the specific unit well L of the multi well plate kit 420' into the unit well inserting groove 713, is performed, and after the second magnetic field applying step S130, a removing step S140 is performed.

The removing step S140, which is a second removing step removing a mixture except for the magnetic particles and proteins coupled with the magnetic particles using the pipettes 141 and 142 in a state in which the magnetic particles having proteins attached thereto in the mixture mixed with the second protein expression are attached to an inner wall of the lower portion of the specific unit well L of the multi well plate kit 420' by a magnetic field applied to the lower portion of the specific unit well L of the multi well plate kit 420', is performed, and after the second removing step S140, a washing step S150 is performed.

The washing step S150, which separates impurities except for the target protein from the magnetic particle by injecting a washing solution injected into the unit well of the multi well plate kit 420 into the specific unit well L of the multi well plate kit 420' using the pipettes 141 and 142 in a state in which the magnet mounting part 710 is lifted down, is performed, and after the washing step S150, a removing step S170 is performed.

The removing step S170, which is a third removing step removing a mixture except for the magnetic particles having the target proteins attached thereto in the mixture mixed with the washing solution using the pipettes 141 and 142 in a state in which the magnetic particles having the target proteins attached thereto in the mixture mixed with the washing solution are attached to an inner wall of the lower portion of the specific unit well of the multi well plate kit 420' by a magnetic field applied to the lower portion of the specific unit well of the multi well plate kit 420', is performed, and after the removing step S170, a target protein separating step S180 is performed.

The washing step S150 washing impurities except for the target protein and the removing step S170 removing the mixture except for the magnetic particles having the target proteins attached thereto may be sequentially performed once or more times, and after the washing step 150, a third magnetic field applying step S160 may be further performed.

The further performed third magnetic field applying step S160 applies a magnetic field to the lower portion of the specific unit well L of the multi well plate kit 420' from the magnet mounting part 710 by lifting up the magnet mounting part 710 so as to insert the lower portion of the specific unit well L of the multi well plate kit 420' into the unit well inserting groove 713.

The target protein separating step S180 performed after the removing step S170 separates the target protein by injecting a target protein eluting solution injected into the unit well of the multi well plate kit 420 into the specific unit well L of the multi well plate kit 420' using the pipettes 141 and 142 in a state in which the magnet mounting part 710 is lifted down, and after the target protein separating step S180, a fourth magnetic field applying step S190 may be further performed.

The further performed fourth magnetic field applying step S190 applies a magnetic field to the lower portion of the specific unit well of the multi well plate kit 420' from the magnet mounting part 710 by lifting up the magnet mounting part 710 so as to insert the lower portion of the specific unit well L of the multi well plate kit 420' into the unit well inserting groove 713 and after the fourth magnetic field applying step S190, a target protein containing solution obtaining step S200 is performed.

The target protein containing solution obtaining step S200 may obtain the target protein containing solution which is a mixture except for the magnetic particles in the protein eluting solution containing the target protein separated from the magnetic particle using the pipettes 141 and 142 in a state in which the magnetic particles in the target protein eluting solution containing the target protein separated from the magnetic particle are attached to an inner wall of the lower portion of the specific unit well L of the multi well plate kit 420' by a magnetic field applied to the lower portion of the specific unit well L of the multi well plate kit 420' to produce the target protein.

In the present invention, the target protein containing solution obtaining step S200 may include injecting the target protein containing solution into a protein storage tube 442-3 mounted on the base plate 400 using the pipettes 141 and 142.

In the present invention, the magnetic particle may be a magnetic particle coupled with an affinity tag of the target protein, and more particularly, may include a metal ion, preferably, may be a magnetic particle coupled with an nickel ion.

According to the present invention, up to 16 kinds of target proteins may be synthesized and produced within 6 hours by combining the method for purification proteins using the magnetic particle with the method for expressing the cell-free protein and applying the combined methods to the automatic biological material purification apparatus including a heating part and a magnetic field applying part.

Advantageous Effects

The method for producing proteins according to the present invention uses the automatic biological material purification apparatus including: a well plate kit; a heating part; and a magnetic field applying part, such that a plurality of target proteins may be more quickly and simply obtained as compared to target proteins obtained by using the existing method for expressing/purifying proteins through conventional cell culture, and a reproducible synthesis efficiency on the same proteins may be obtained due to no deviation between reaction wells.

(Column G: Well region having a cell-free protein expression solution, Column H: Well region having a DEPC dilution water, Column L: Well region having a template for cell-free protein synthesis, Column A to D: Well region having a magnetic particle reaction solution and a washing solution for coupling a target protein with the magnetic particles, Column E: Well region having a target protein elution, and Column F: Well region having magnetic particles for attaching the target protein)

Figure 11:
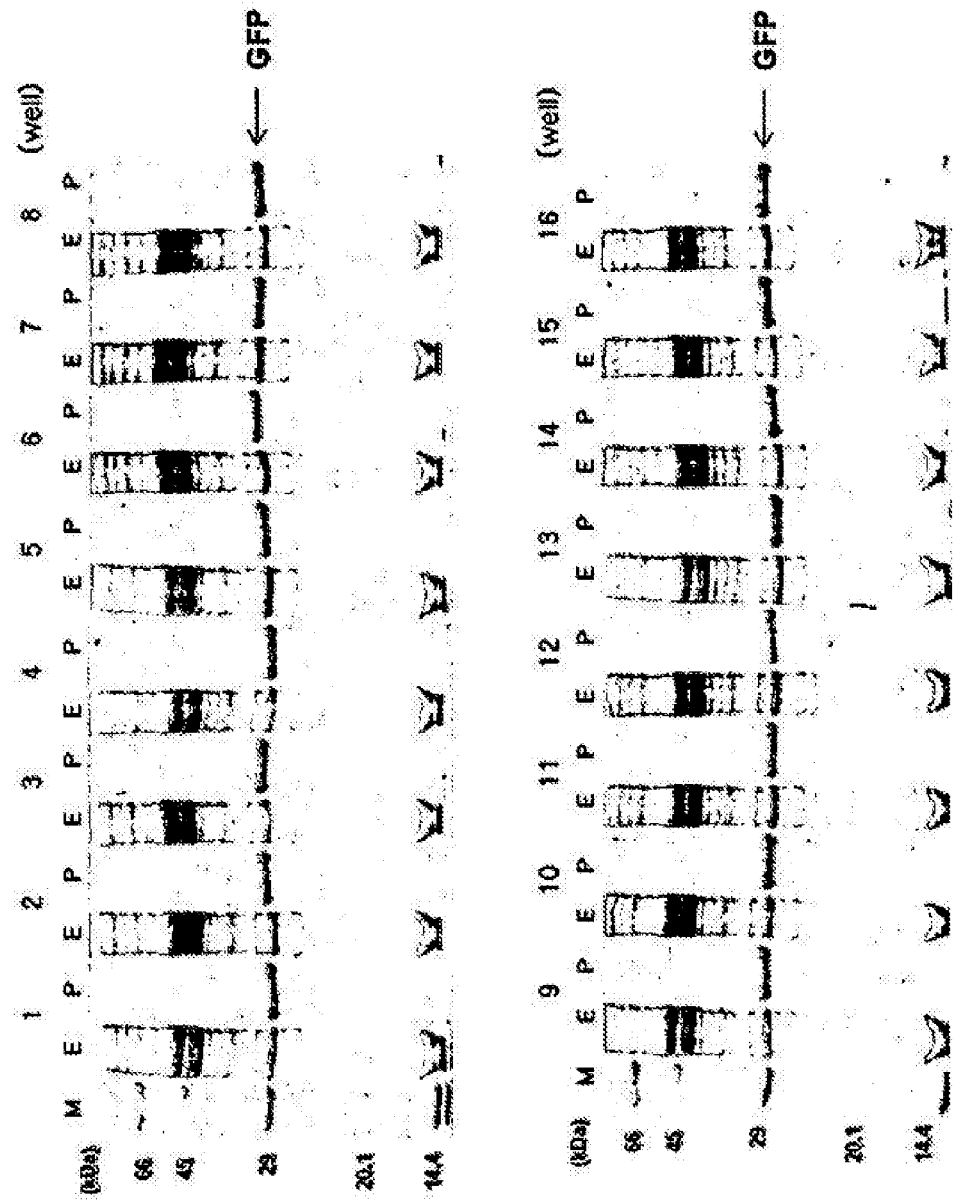

FIG. 11 shows a result of a SDS-PAGE gel of target proteins (GFPs) produced by using a method for producing proteins according to the present invention; and (M: AccuLadder™ Protein Size Marker (Low) of Bioneer Corporation, E: expressed GFP sample, P: purified GFP sample, 1~16: GFP synthesis protein reacted in each unit well)

Figure 12:
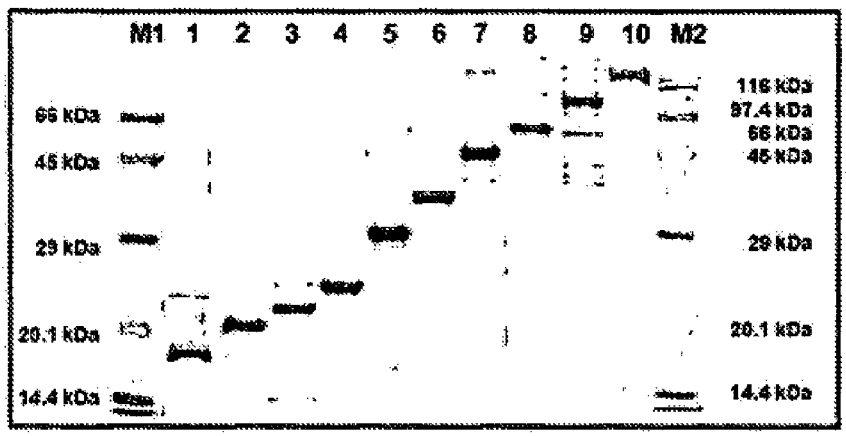
Figure 12:
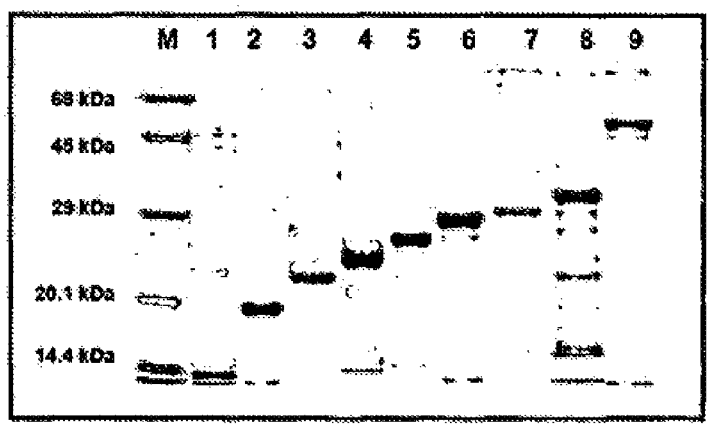

FIG. 12 shows a result of SDS-PAGE gel of target proteins for various template DNAs produced by using a method for producing proteins according to the present invention.

DETAILED DESCRIPTION OF MAIN ELEMENTS

100: pipette BLOCK 110: SYRINGE PIN HOLDER
112: INFORMATION GUIDE 120: SYRINGE PIN
130: SYRINGE PIN GUIDE BLOCK 131: SYRINGE PIN GUIDE HOLE
133: pipette MOUNTING PART 133-1: COMMUNICATING HOLE
133-2: ADHESION RING 134: pipette MOUNTING PART
134-1: COMMUNICATING HOLE 134-2: ADHESION RING
141: pipette 142: pipette
150: SYRINGE PIN GUIDE BLOCK SUPPORTING PLATE 152: UP-AND-DOWN MOVING NUT
160: GUIDE ROD
171: SYRINGE PIN CONTROL MOTOR SUPPORTING PLATE
172: SYRINGE PIN CONTROL MOTOR
173: SYRINGE PIN CONTROL SCREW
181: UPPER DESORPTION PLATE 182: DESORPTION PLATE
183: CONNECTION ROD 184: PROTRUSION ROD
185: SPRING 200: FIXED MAIN BODY
231: UP-AND-DOWN MOVING MOTOR
232: UP-AND-DOWN MOVING BELT
233: UP-AND-DOWN MOVING SCREW
241: BACK-AND-FORTH MOVING SLIDER
300: CASING 310: BACK-AND-FORTH MOVING SUPPORT ROD
311: BACK-AND-FORTH GUIDER 350: DOOR
320: BACK-AND-FORTH MOVING MOTOR
330: BACK-AND-FORTH MOVING BELT
340: ULTRAVIOLET LAMP 360: TOUCH SCREEN
400: BASE PLATE 401: DOORKNOB
420': MULTI WELL PLATE 420: MULTI WELL PLATE
430: pipette RACK 440: PROTEIN STORAGE TUBE RACK
450: WASTE tray
442-1: CELL DISRUPTED LIQUID STORAGE TUBE
442-3: PROTEIN STORAGE TUBE
700: MAGNETIC FIELD APPLYING PART
710: MAGNET MOUNTING PART 711: MAGNET
713: UNIT WELL INSERTING GROOVE
720: MAGNET MOUNTING PART SUPPORT
730: GUIDE ROD 740: GUIDE BLOCK
750: TENSION SPRING 760: LIFTING PART
761: LIFTING MOTOR 762: FIRST LIFTING SHAFT
763: LIFTING CAM 764: SECOND LIFTING SHAFT
780: HEIGHT SENSOR 781: SENSING PART
782: SENSING TARGET PART 810: HEATING PART
812: HEATING PART FIXING PLATE

BEST MODE

Hereinafter, although the present invention will be described in detail with reference to the following Examples, which has been disclosed for illustrative purposes, it will be apparent to those skilled in the art that modifications and variations can be made without being limited by the following Examples. Materials and methods used in Examples of the present invention are as follows.

EXAMPLE 1

Preparation of Template DNA (1) Preparation of Plasmid DNA

A template DNA-plasmid DNA was prepared for protein synthesis. Each gene was synthesized by a method for gene synthesis (*NBiochem. Biophys. Res. Commun.* 1998, 248, 200-203), followed by treatment with a restriction enzyme, and cloning into an expression vector for *E. coli*.

As the expression vector for *E. coli*, pBIVT (Bioneer Corporation, Korea), pIVEX (Roche, Germany), pET (Novagen, Germany), pK7, pQE, and the like, may be used, but the present invention is not limited thereto.

In addition, the expression vector for *E. coli*, an affinity tag should be included in the expression vector. In the present Example, the expression vector including a histidine tag was used, and but the present invention is not limited thereto and thus, the expression vector may include another tag.

In the present Example, CalmL3, RNaseH, DUSP3, CAT, AcGFP, EF-Ts, VF, Poly A polymerase, MMLV RTase, BM3, gene were used.

More specifically, for the treatment with the restriction enzyme on a gene synthesis material, 1 μl of BamHI (Bioneer Corporation, Korea), 1 μl of NotI (Bioneer Corporation, Korea), 2 μl of 10× AccuCut™ buffer (Bioneer Corporation, Korea), 10 μl of gene synthesis material and 6 μl of sterile distilled water were added to each tube, mixed together, and disposed at a constant temperature of 37° C. for three hours. For the treatment with the restriction enzyme on an expression vector for E. coli, 1 μl of BamHI (Bioneer Corporation, Korea), 1 μl of NotI (Bioneer Corporation, Korea), 2 μl of 10× AccuCut™ buffer (Bioneer Corporation, Korea), 10 μl of expression vector for E. coli and 6 μl of sterile distilled water were added to each tube, mixed together, and disposed at a constant temperature of 37° C. for three hours. DNA was extracted from each reactant treated with each restriction enzyme using Accuprep Gel Extraction kit (Bioneer Corporation, Korea).

5 μl of 2× rapid ligation buffer (Promega Corporation, US), 1 μl of T4 DNA ligase (Promega Corporation, US), 3 μl of restriction enzyme treatment gene synthesis material, 1 μl of restriction enzyme treatment vector were added to a tube, mixed together, and disposed at a constant temperature of 16° C. for one hour. Then, 10 μl of the reaction solution disposed at constant temperature was put into 100 μl of E. coli competent cell, the mixture was placed on ice for 30 minutes and cultured at 42° C. for 90 seconds, and then placed again on ice for 5 minutes. The reactant was inoculated into a LB plate containing kanamycin and cultured at 37° C. for 16 hours.

After white colony was taken and cultured in 10 ml of LB liquid medium for 16 hours, followed by centrifugation, the thus-obtained supernatant was removed and plasmid DNA was extracted from pellet using AccuPrep plasmid DNA prep kit (Bioneer Corporation, Korea). It was confirmed by sequencing whether or not the extracted DNA was gene synthesized by each gene synthesis method, and as DNA to be used for protein synthesis, corresponding colony was cultured to secure plasmid DNA by the same method. Concentration and purity of the plasmid DNA were measured by UV spectrometer (Shimazu Corporation, Japan) and it was confirmed that the plasmid DNA had a purity of 1.8 to 2.0.

(2) Preparation of PCR Product

Figure 7:
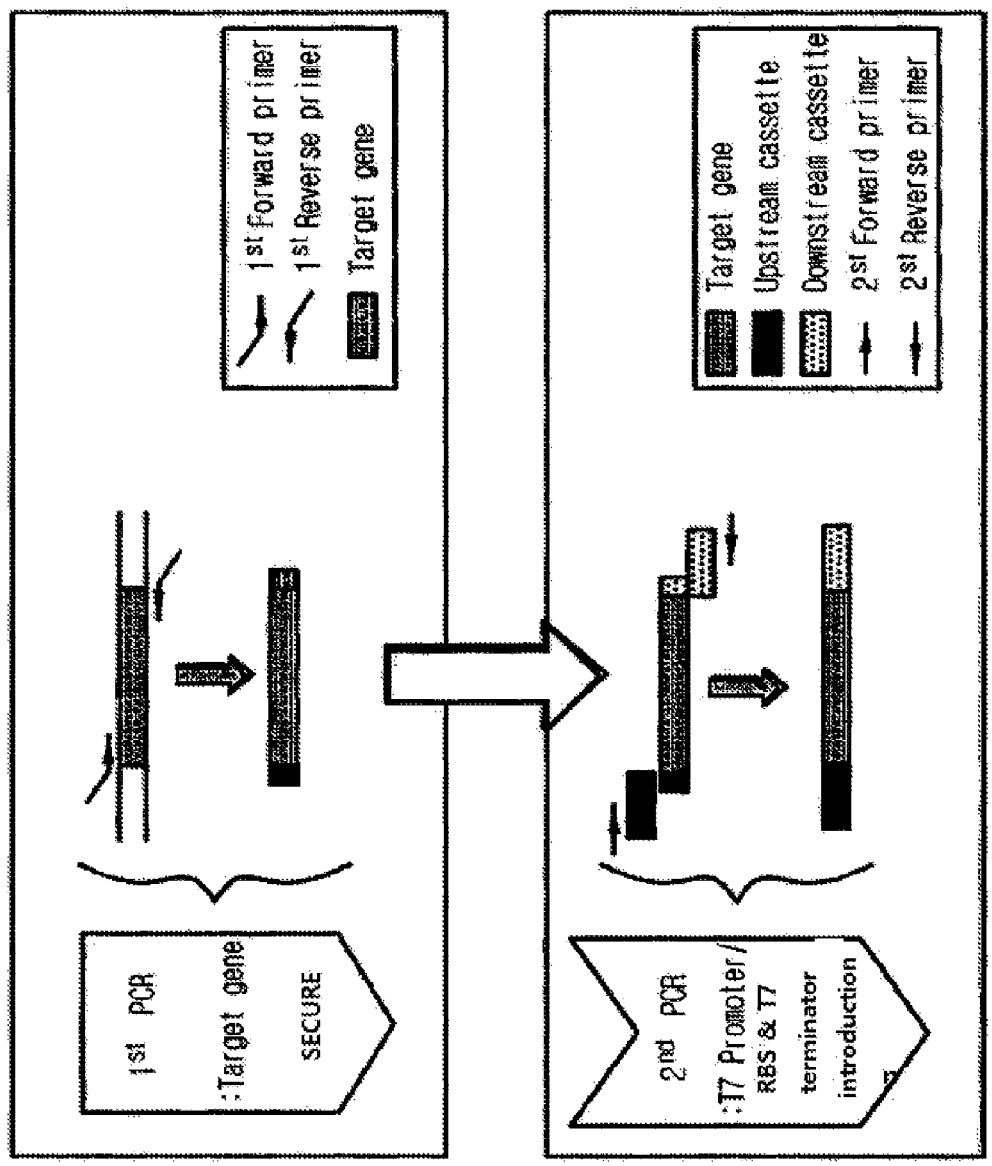
FIG. 7 shows a manufacturing diagram of a template PCR product for producing proteins using the automatic biological material purification apparatus including a heating part and a magnetic applying part according to the present invention.

A template DNA-PCR product was prepared for protein synthesis. A 'kit for PCR' using two-step PCR principle has been developed for preparation of PCR product, and a method for preparing PCR product is shown in FIG. 7 and kit components are shown in the following Table 1.

TABLE 1

| Kit for PCR |
|---|
| AccuPower ® PCR Premix |
| N terminus upstream cassette |
| N terminus downstream cassette |
| C terminus upstream cassette |
| C terminus downstream cassette |
| $2^{nd}$ Forward primer |
| $2^{nd}$ Reverse primer |

More specifically, a target gene was firstly capable of being amplified, a primer set having overlapping sequences at 5' and 3' terminals was fabricated, and a first PCR reaction was performed with a sample having target gene (genomic DNA, T vector, and the like) as a template. In order to perform PCR reaction, AccuPower PCR Premix provided in a kit was used and the reaction under reaction conditions including denaturalization at 94° C. for 5 minutes and amplification at 94° C. for 30 seconds, at 58° C. for 30 seconds and at 72° C. for 1 minute as one cycle was performed thirty times, and then polymerization was finally performed at 72° C. for 5 minutes. Then, a primary PCR reactant was refined using AccuPrep PCR refinement kit (Bioneer Corporation, Korea) or AccuPrep Gel Extraction kit (Bioneer Corporation, Korea).

A secondary overlapping PCR was performed using the primary PCR reactant as a template to finally synthesize a PCR product for protein synthesis. In order to perform the PCR reaction, a cassette set and a primer set provided in a kit of Table 1 above and the primary PCR reactant were added and the reaction under the reaction conditions including denaturalization at 94° C. for 5 minutes and amplification at 94° C. for 30 seconds, at 58° C. for 30 seconds and at 72° C. for 1 minute as one cycle was performed thirty times, and then polymerization was finally performed at 72° C. for 5 minutes. A secondary PCR reactant was refined using AccuPrep Gel Extraction kit (Bioneer Corporation, Korea).

The upstream cassette and downstream cassette as provided above are oligonucleotides encoding an affinity tag coupled to the target protein, and more preferably, they include a histidine tag.

EXAMPLE 2

Preparation of Cell Disrupted Liquid for Protein Expression (1) Cell Culture

First, E. coli [BL21(DE3) (Novagen Corporation, US)] was cultured in 350 l fermenter (2× YT medium) at 37° C. Then, at absorbance (OD 600) of 0.5, 1 mM IPTG was added to express T7 RNA polymerase, and at absorbance (OD 600) 3.0 to 6.0, culturing was terminated and cells were recovered by centrifugation and stored at −50° C.

(2) Preparation of Cell Disrupted liquid

The recovered E. coli 100 g was added to 500 ml of washing solution [10 mM Tris(oAc) pH 8.2, 14 mM Mg(oAc)$_2$, 60 mM K(OAc), 1 mM DTT (dithiothreitol), and 0.05% (v/v) 2-mercaptoethanol (2-ME)] and well-washed, followed by centrifugation (3,000 RPM, 30 minutes), and the above-described procedures were repeated three times. After washing and measuring E. coli mass, a buffer solution [2-ME was removed from the washing solution] having a volume 1.1 times larger than the mass was added, E. coli was uniformly mixed, and then cells were disrupted under a constant pressure (160 to 280 MPa) using a pressure cell homogenizer (Stansted Fluid Power).

The cell disrupted liquid was separated by high speed centrifugation (16,000 RPM, 30 minutes, 4° C.) to recover supernatant, and a pre-culture solution [293.3 mM Tris(OAc) pH 8.2, 2 mM Mg(OAc)$_2$, 10.4 mM ATP, 200 mM creatine phosphate, 4.4 mM DTT, 0.04 mM amino acids, and 26.7 g/ml creatine kinase] was added to the cell disrupted liquid, wherein 3 ml of the pre-culture solution was used per 10 ml of the cell disrupted liquid, followed by culturing at 37° C. for 90 minutes, thereby preparing a pre-cultured solution. In addition, after the pre-cultured solution was put into a dialysis tube (10 kDa, Dialysis Tubing, Sigma Corporation, US), and dialyzed four times in buffer solution having 20 times volume at 4° C. for 45 minutes, thereby removing foreign materials after the pre-culture, and a solution in the dialysis tube was subjected to centrifugation (11,000 RPM, 20 minutes, 4° C.), and cell disrupted liquid for protein synthesis was prepared. The cell disrupted liquid was stored at −70° C. before fabricating a multi well plate kit.

EXAMPLE 3

Preparation of Cell-Free Protein Expression Solution

A protein expression solution required for cell-free protein synthesis was prepared.

More specifically, the cell-free protein expression solution [114 mM Hepes-KOH (pH 8.2), 2.4 mM ATP, each of 1.7 mM CTP, GTP and UTP, 2 mM DTT, 90 mM K (Glu), 80 mM NH4(OAc), 12 mM Mg(OAc), 68 g/ml folinic acid (L-5-formyl-5,6,7,8-tetrahydrofolic acid), each of 1.5 mM 20 amino acids, 2% PEG 8000, and 67 mM creatine phosphate] was prepared. The expression solution was stored at −20° C. before fabricating a multi well plate kit.

EXAMPLE 4

Preparation of Magnetic Particle Reaction Solution and Washing Solution

A magnetic particle used for protein purification is a magnetic particle obtained by coating Fe particles having magnetism with silica and complexing an end thereof with nickel (Ni). The magnetic particle is commercially available from Sigma Corporation, Promega Corporation, Qiagen Corporation, and the like. The magnetic bead has advantages in that protein is capable of easily refined using magnetic properties, thereby making it possible to be used in various fields.

The magnetic particle reaction solution for coupling the target protein with the magnetic particles required for extraction of the target protein and the washing solution were prepared. More specifically, the magnetic particle reaction solution and the washing solution [50 mM HEPES-KOH (pH7.5), 300 mM NaCl, 10 mM Imidazole, 5 mM 2-mercaptoethanol (2-ME) and 10% (v/v) glycerol] were prepared. The solutions was stored at 4° C. before fabricating a multi well plate kit.

EXAMPLE 5

Preparation of Protein Eluting Solution

A protein eluting solution required for purification of the target protein was prepared.

More specifically, a protein eluting solution [50 mM HEPES-KOH (pH7.5), 300 mM NaCl, 1 M Imidazole, 5 mM 2-mercaptoethanol (2-ME), 10% (v/v) glycerol] were prepared. The solutions was stored at 4° C. before fabricating a multi well plate kit.

EXAMPLE 6

Manufacture of Multi Well Plate Kit (1) Division and Storage of Cell Disrupted Liquid The stored cell disrupted liquid prepared by Example 2 above was completely melted on an ice. The completely melted cell disrupted liquid was divided into 8-strip tube for 200 μl each, and stored at −70° C.

(2) Manufacture of Multi Well Plate Kit

Multi well plate kits were manufactured using solutions prepared by Examples 3 to 5 above.

Figure 10:
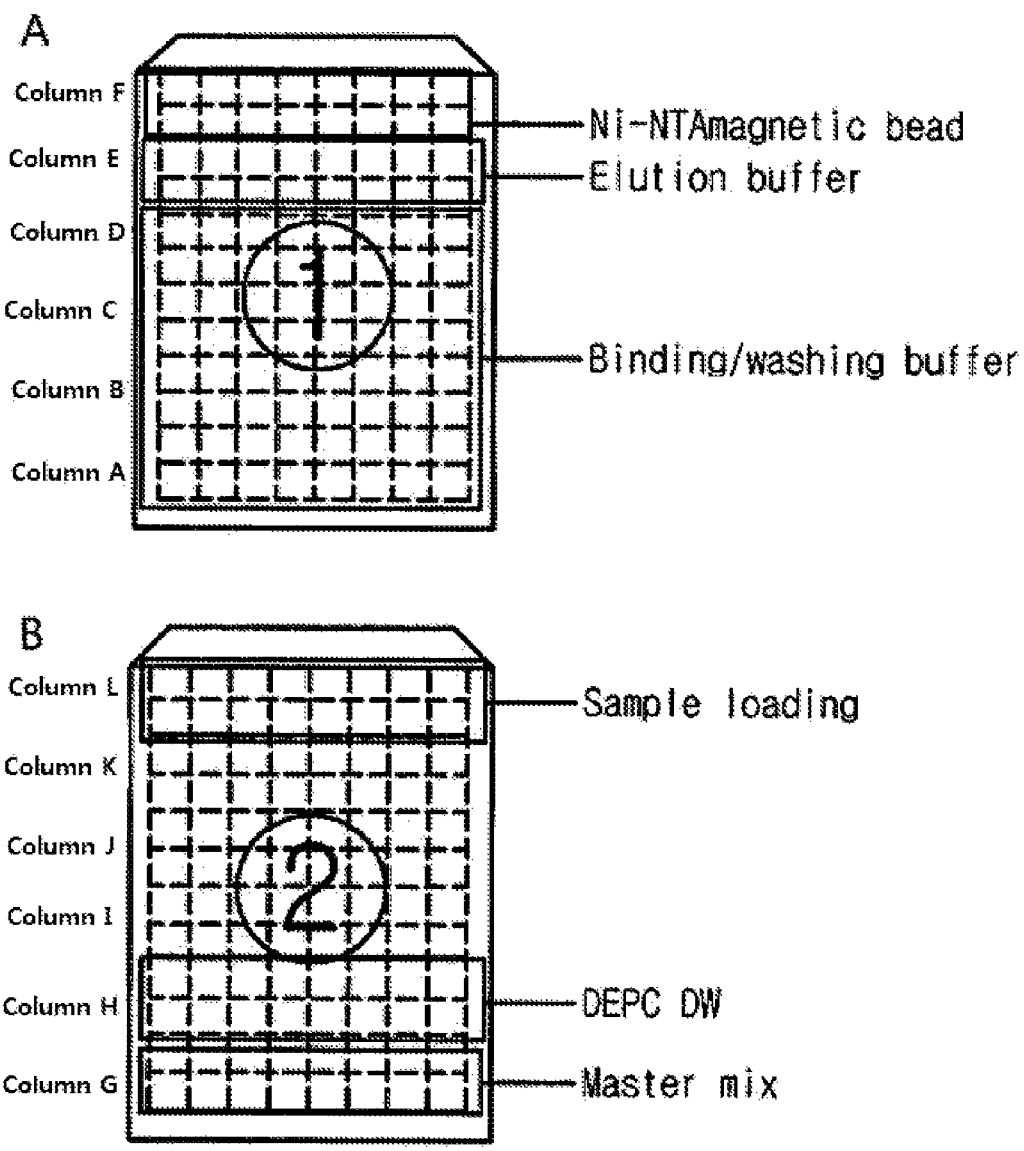
FIG. 10 shows a first multi well plate kit (A) and a second multi well plate kit (B) used in the automatic biological material purification apparatus including a heating part and a magnetic applying part according to the present invention.

First, referring to B of FIG. 10, a second multi well plate kit 420' was manufactured. More specifically, after the cell-free protein expression solution prepared by Example 3 above was completely melted on an ice, a protein expression solution of 350 μl was divided into each portion of column G of the multi well plate, a DEPC distilled water (Bioneer Corporation, Korea) of 200 μl was divided into each portion of column H thereof shown in B of FIG. 10, and then, an upper portion of the multi well plate was sealed with a film and stored at −20° C.

Then, referring to A of FIG. 10, a first multi well plate kit 420 was manufactured. More specifically, the magnetic particle reaction solution and the washing solution prepared in Example 4 above of 1.2 ml were divided into each portion of columns A to D of the multi well plate 1 shown in A of FIG. 10, and the protein eluting solution of 250 μl was divided into each portion of column E. In addition, a solution containing magnetic particles coupled with an nickel ion (Bioneer Corporation, Korea) of 500 μl was divided into each portion of column F, and then, an upper portion of the multi well plate was sealed with a film and stored at 4° C.

EXAMPLE 7

Method for Expressing/Purifying Protein Using Automatic Biological Material purification Apparatus Including Heating Part and Magnetic Field Applying Part (1) Preparation for Protein Synthesis As an automatic biological material purification apparatus including a heating part and a magnetic field applying part used in the present invention, an apparatus disclosed in Korean Patent No. KR 10-1025135, Korean Patent Laid-Open Publication No. 10-2011-0081718, and the like, may be used or ExiProgen™ (Bioneer Corporation, Korea) may be used, but the present invention is not limited thereto. In the present experiment, ExiProgen™ (Bioneer Corporation, Korea) was used.

Figure 9:
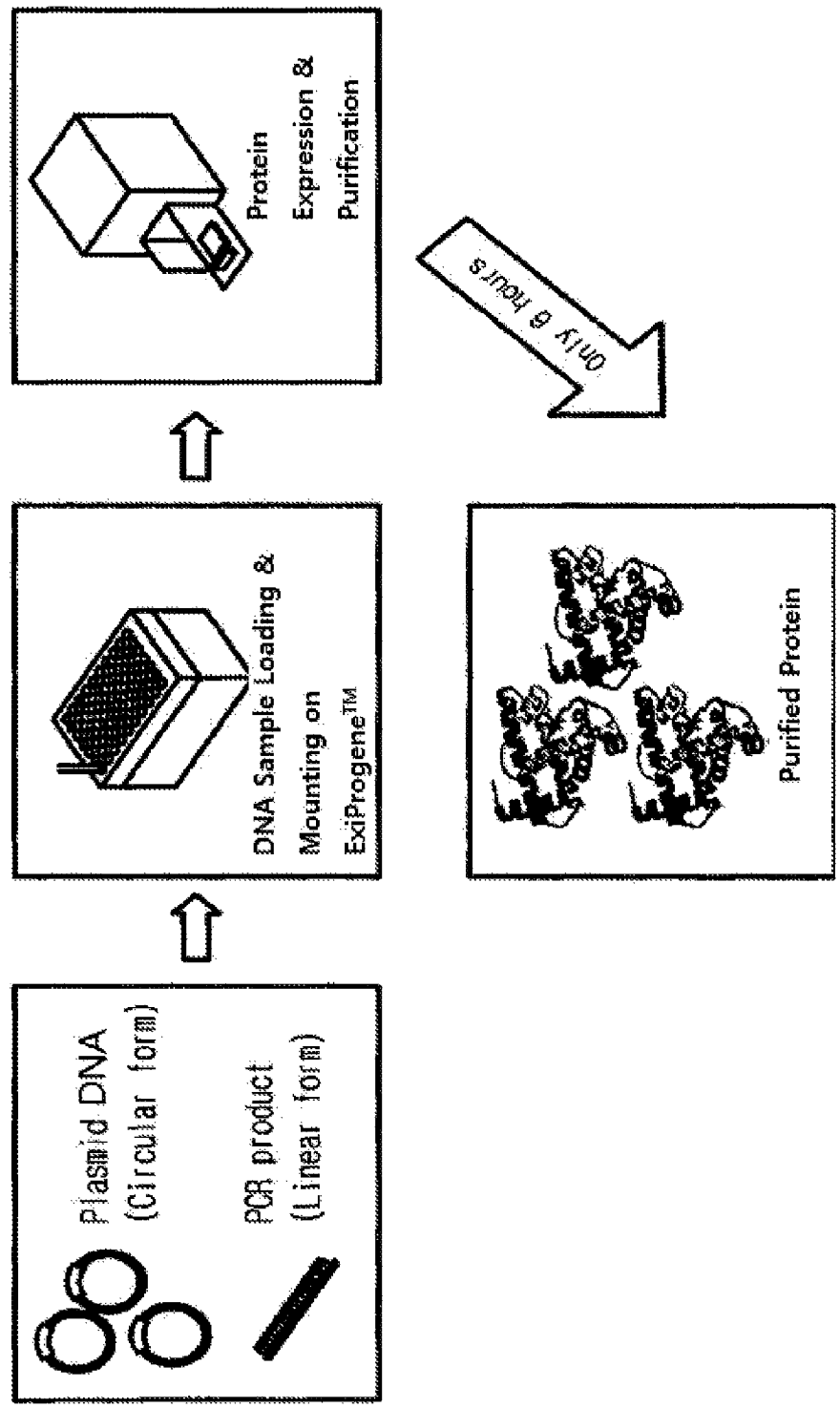
FIG. 9 is a diagram of an experiment using an automatic biological material purification apparatus including a heating part and a magnetic applying part according to the present invention.

A method for expression/purifying protein using an automatic biological material purification apparatus including a heating part and a magnetic field applying part was performed as shown in FIG. 9. More specifically, the tube having the divided cell disrupted liquid prepared by step (1) of Example 6 and the multi well plate kit were taken out from fridge to be completely melted at room temperature. Then, first and second multi well plates were punched using 6 Hole Puncher which is provided with ExiProgen™ (Bioneer Corporation, Korea), the automatic biological material purification apparatus including a heating part and a magnetic field applying part.

The template DNA prepared by Example 1 was added to column L of the second multi well plate 420'. Then, the cell disrupted liquid and the multi well plates were mounted on corresponding positions of ExiProgen™ (Bioneer Corporation, Korea). After elution tube to be filled with the protein purification solution and a filter tip were put into corresponding racks and mounted on positions of the corresponding racks, a set up tray was pushed therein, and a door of the apparatus was closed. ExiProgen™ (Bioneer Corporation, Korea) was turned on and protocol 902 was practiced.

Here, an amount of the template DNA to be added may vary depending on kinds and sizes of the template DNA, preferably, in the case of plasmid DNA, 1 to 10 ug was used, and in the case of PCR product, 500 ng to 2 ug was used.

Figure 8:
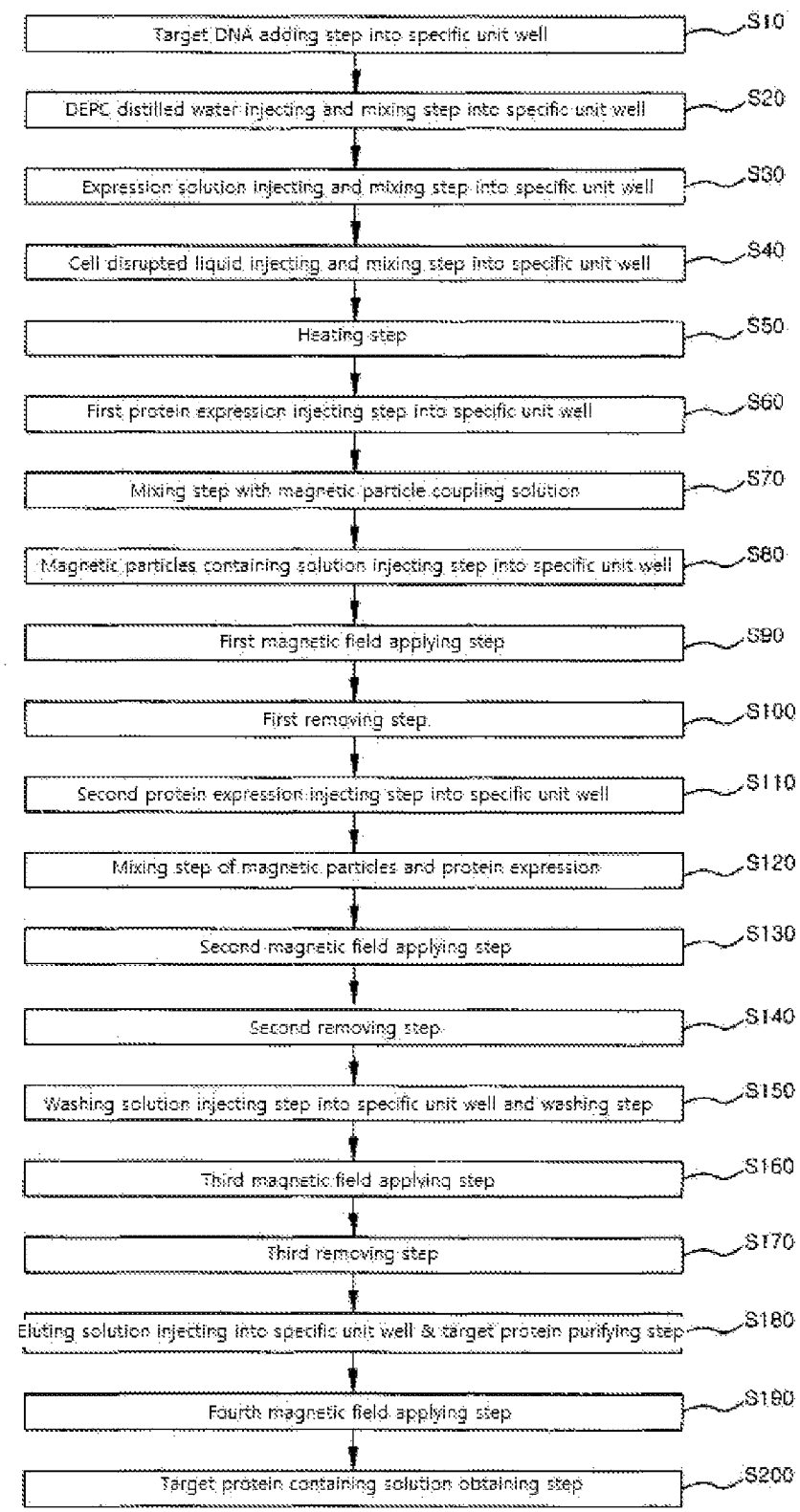
FIG. 8 is a diagram of a method for producing proteins using the automatic biological material purification apparatus including a heating part and a magnetic applying part according to the present invention.

(2) Process for Expressing/Purifying Protein Using Automatic Biological Material purification Apparatus Including Heating Part and Magnetic Field Applying Part FIG. 8 is a diagram of a method for producing proteins simultaneously performing expression and purification of target protein using an automatic biological material purification apparatus including a heating part and a magnetic applying part.

Figure 5:
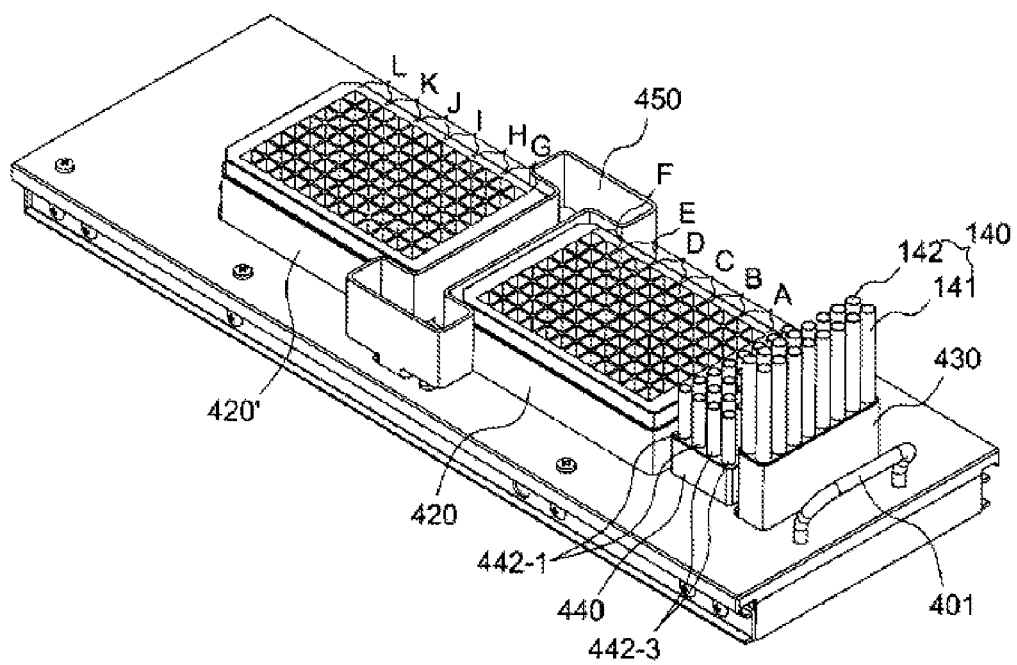
FIG. 5 shows a state in which a base plate of the automatic biological material purification apparatus including a heating part and a magnetic applying part according to the present invention is used.

Referring to FIGS. 5 and 8, an injecting step S10 of target DNA as a template for cell-free protein synthesis into the specific unit well was provided. Referring to B of FIG. 10, DNA was added to a unit well L of the multi well plate 420' in the injecting step S10 of target DNA.

Figure 1:
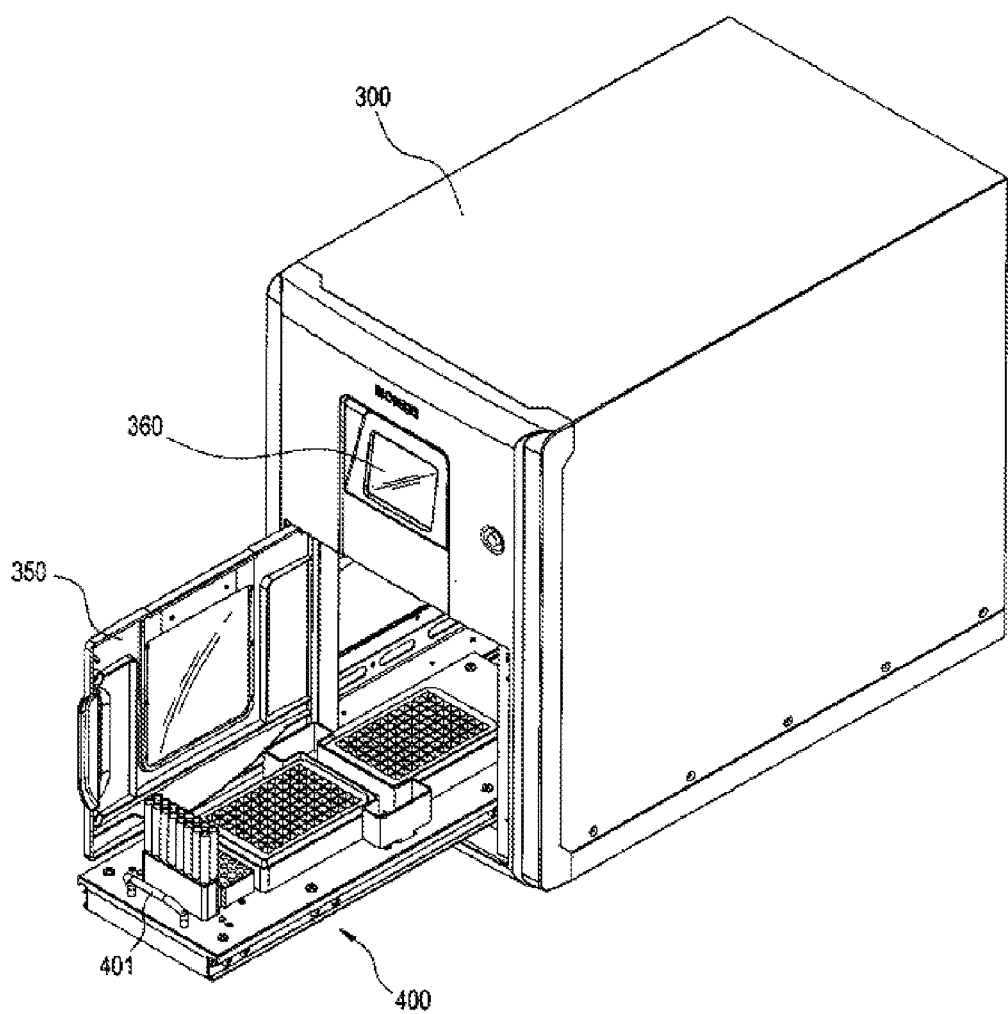
FIG. 1 shows a state in which a base plate of an automatic biological material purification apparatus including a heating part and a magnetic applying part according to the present invention inserts a casing.
Figure 2:
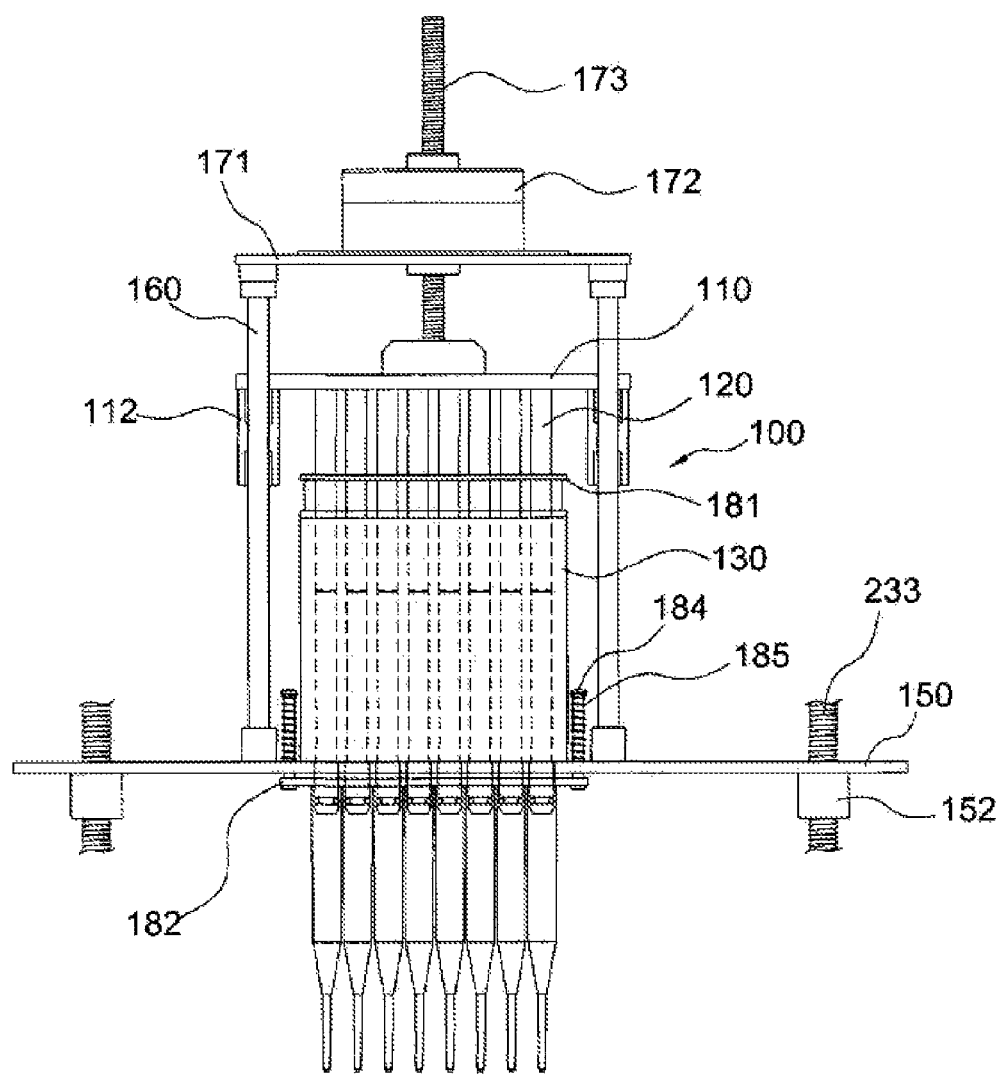
FIG. 2 schematically shows a pipette block of the automatic biological material purification apparatus including a heating part and a magnetic applying part according to the present invention.
Figure 3:
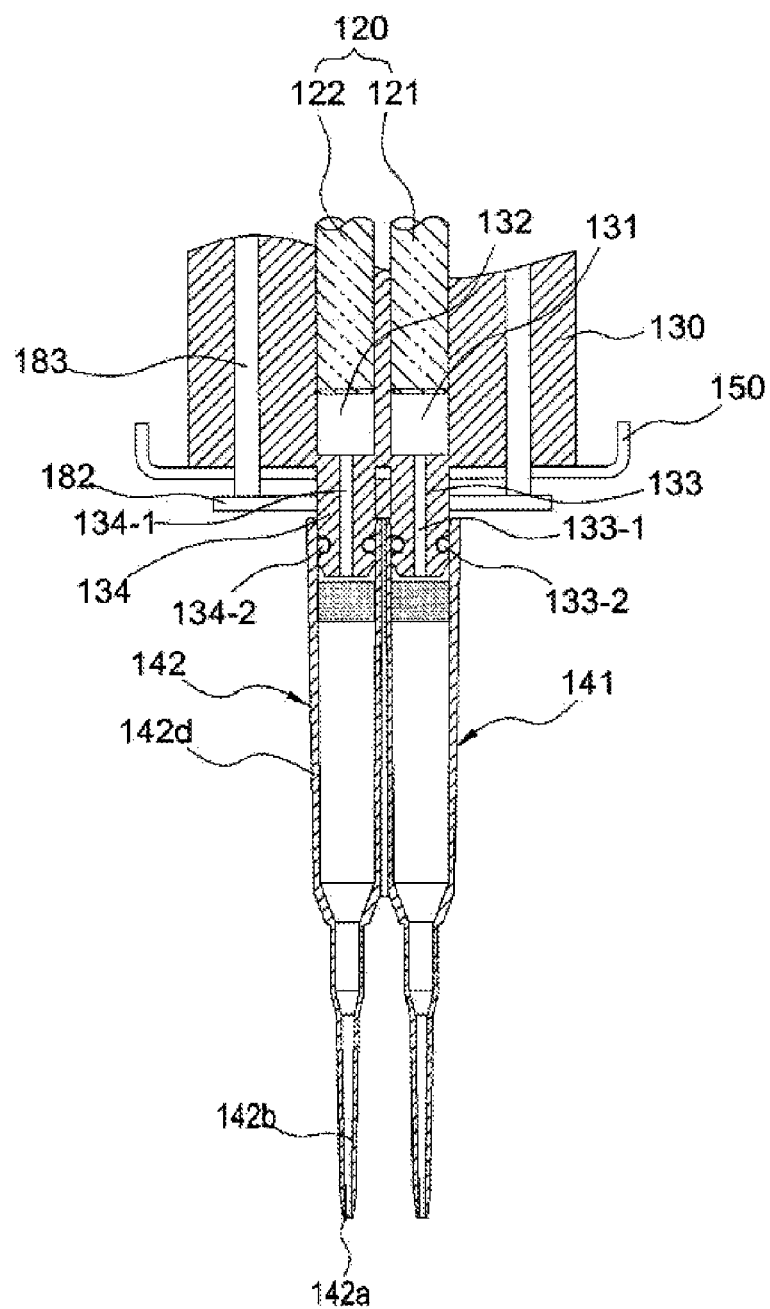
FIG. 3 is a cross-sectional view of a main part of the pipette block of the automatic biological material purification apparatus including a heating part and a magnetic applying part according to the present invention.
Figure 4:
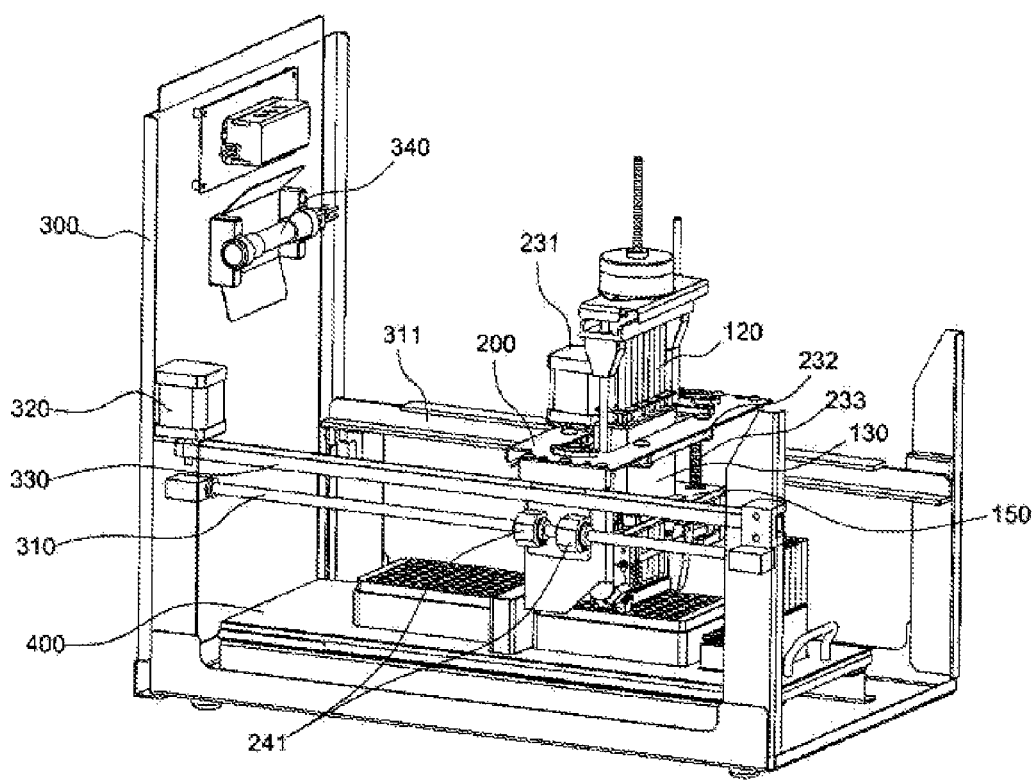
FIG. 4 is a perspective view in which a casing is partially removed from the automatic biological material purification apparatus including a heating part and a magnetic applying part according to the present invention.

Referring to FIGS. 5 and 8, a first mixing step S20 mixing by injecting a DEPC distilled water into the specific unit well was provided. In the mixing step by injecting the DEPC distilled water into the specific unit well, the DEPC distilled water injected into a unit well H of the multi well plate 420' was injected into the specific unit well L using pipettes 141 and 142 (see FIG. 3). Accordingly, the DEPC distilled water was mixed with the target DNA injected into the specific unit well L.

Referring to FIGS. 5 and 8, a second mixing step S30 mixing by injecting a cell free protein expression solution into the specific unit well was provided. In the second mixing step S30, the cell free protein expression solution injected into a unit well G of the multi well plate 420' was injected into the specific unit well L using pipettes 141 and 142. Accordingly, the cell free protein expression solution was mixed with the target DNA solution in the specific unit well L.

Referring to FIGS. 5 and 8, a mixture preparing step S40 mixing by injecting a cell disrupted liquid into the specific unit well was provided. In the mixture preparing step S40, the cell disrupted liquid injected into a tube 442-1 (see FIG. 5) injected with the cell disrupted liquid was injected into the specific unit well L using the pipettes 141 and 142. Accordingly, the cell disrupted liquid was mixed with the mixture of the target DNA and the cell free protein expression solution in the specific unit well L, thereby preparing a protein synthesis reaction solution.

Figure 6:
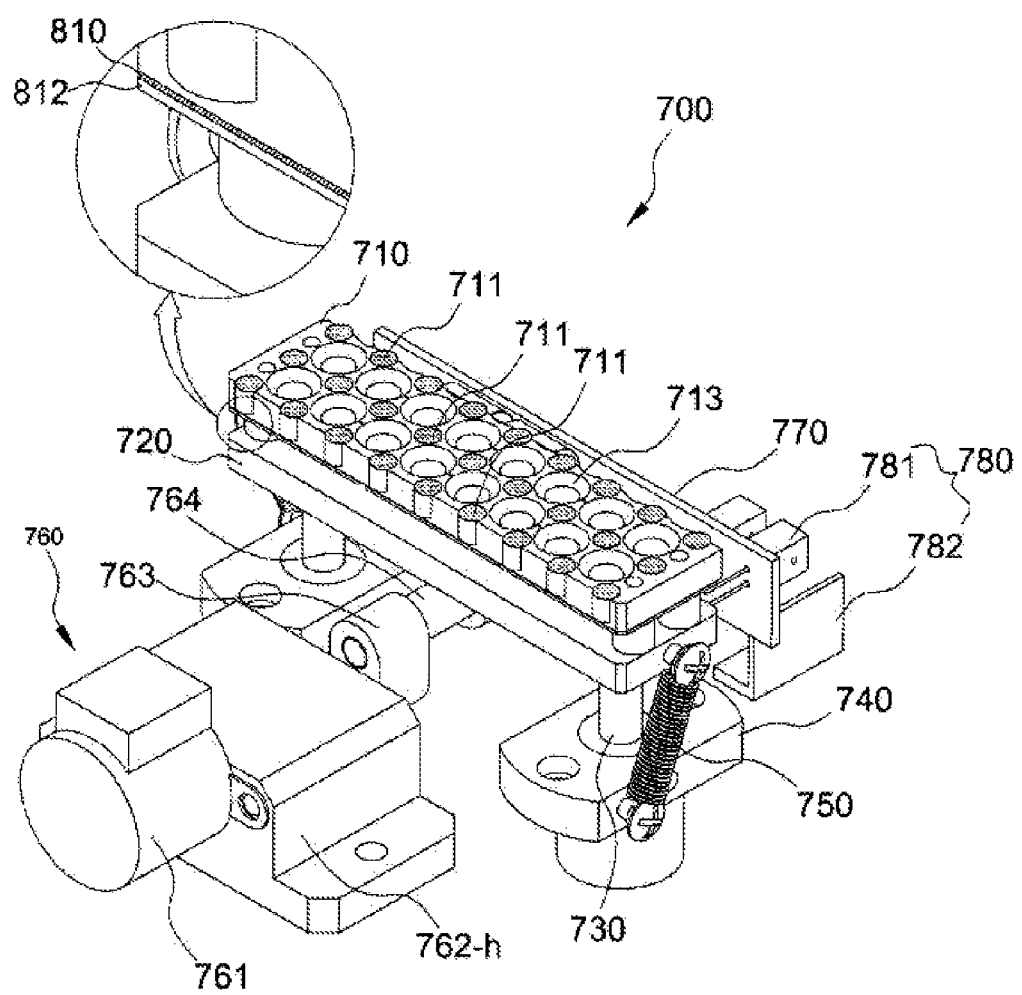
FIG. 6 is a perspective view of a magnetic mounting part and a lifting part of the automatic biological material purification apparatus including a heating part and a magnetic applying part according to the present invention.

Referring to FIGS. 5 and 8, a first heating step S50 was provided. In the heating step S50, a state in which the lower portion of the specific unit well L of the multi well plate kit 420' inserted a unit well inserting groove 713 (see FIG. 6) by lifting up the magnet mounting part 710 (see FIG. 6) was provided. Then, expression of protein in the prepared protein synthesis reaction solution is promoted by heating a lower portion of the specific unit well L using the heating part 720 (see FIG. 6). In the heating step S50, the reaction is activated due to enzymes in the mixture to achieve RNA synthesis from target DNA and protein expression. The lower portion of the specific unit well L may be heated at 30° C. for 3 hours by the heating part.

Referring to FIGS. 5 and 8, a first protein expression injecting step S60 into the specific unit well was provided. In the first protein expression injecting step S60, the protein expressed mixture from the specific unit well L after the first heating step S50 was injected into a unit well J of the multi well plate 420' using the pipettes 141 and 142.

Referring to FIGS. 5 and 8, a third mixing step S70 mixing the magnetic particle reaction solution and the magnetic particles is provided. In the third mixing step S70, the magnetic particle reaction solution injected into a unit well A of the multi well plate 420 was injected into the unit well F of the multi well plate 420 using the pipettes 141 and 142 to be mixed with the magnetic particles. Accordingly, a surface of the magnetic particle was equilibrated by the magnetic particle reaction solution.

Referring to FIGS. 5 and 8, the injecting step of the magnetic particle into the specific unit well, that is, the second injecting step S80 of the mixture mixed with the magnetic particle reaction solution into the specific unit well was provided. In the injecting step S80, the mixture mixed with the magnetic particle reaction solution of the specific unit well F was injected into the specific unit well L using the pipettes 141 and 142 in a state in which the magnet mounting part 710 is lifted down.

Referring to FIGS. 5 and 8, a first magnetic field applying step S90 was provided. In the first magnetic field applying step S90, the lower portion of the specific unit well L inserted the unit well inserting groove 713 by lifting up the magnet mounting part 710. Accordingly, a magnetic field was applied from the magnet 711 (see FIG. 6) mounted on the magnet mounting part to the lower portion of the specific unit well L.

Referring to FIGS. 5 and 8, a first removing step S100 was provided. The first removing step S100 was performed in a state in which a magnetic field is applied to the lower portion of the specific unit well by the first magnetic field applying step S90. More specifically, in the first removing step S100, a state in which the magnetic particles of the magnetic particle reaction solution in the mixture mixed with the magnetic particle reaction solution were attached to an inner wall of the lower portion of the specific unit well L was maintained.

In addition, in the first removing step S100, the reaction solution except for the magnetic particles in the mixture mixed with the magnetic particle reaction solution was removed using the pipettes 141 and 142. The reaction solution removed from the first removing step S100 may be discharged to a waste tray 450 (see FIG. 5). The first removing step S100 was performed, such that the magnetic particles were left in the specific unit well L.

In addition, the injecting step S80 of the reaction solution mixed with the magnetic particles into the specific unit well, the first magnetic field applying step S90, and the first removing step S100 may be repeated once. Here, in the injecting step S80 of the reaction solution mixed with the magnetic particles into the specific unit well, the magnetic particle reaction solution injected into the unit well A of the multi well plate 420 was injected into the specific unit well L. Then, the first magnetic field applying step S90 and the first removing step S100 were performed in the same scheme.

Referring to FIGS. 5 and 8, a second protein expression injecting step S110 into the specific unit well was provided. In the second protein expression injecting step S110, the protein expression of the specific unit well J was injected into the specific unit well L using the pipettes 141 and 142.

Referring to FIGS. 5 and 8, reacting step S120 mixing the second protein expression with the magnetic particles was provided. In the reacting step S120, the second protein expression injected into the specific unit well L was mixed with the magnetic particles using the pipettes 141 and 142. Accordingly, a surface of the magnetic particle was coupled with the protein expression.

Referring to FIGS. 5 and 8, a second magnetic field applying step S130 was provided. In the second magnetic field applying step S130, the lower portion of the specific unit well L inserted the unit well inserting groove 713 by lifting up the magnet mounting part 710. Accordingly, a magnetic field was applied from the magnet mounted on the magnet mounting part 710 to the lower portion of the specific unit well L.

Referring to FIGS. 5 and 8, a second removing step S140 was provided. The second removing step S140 was performed in a state in which a magnetic field is applied to the lower portion of the specific unit well L by the second magnetic field applying step S130. Therefore, in the second removing step S130, a state in which magnetic particles and protein coupled with the magnetic particles in the magnetic particle protein expression were attached to an inner wall of the lower portion of the specific unit well L by a magnetic field was maintained.

In addition, in the second removing step S140, a mixture except for magnetic particles and proteins coupled with the magnetic particles in the magnetic particle protein expression was removed using the pipettes 141 and 142. The mixture removed from the second removing step S140 may be discharged to a unit well K of the multi well plate 420'. The second removing step S140 was performed, such that the magnetic particles and the proteins coupled with the magnetic particles were left in the specific unit well L.

Referring to FIGS. 5 and 8, a washing step S150 separating impurities except for target protein from the magnetic particles by injecting a washing solution into the specific unit well and washing the magnetic particles was provided. In the washing step S150, the washing solution injected into the unit well B of the multi well plate 420 was injected into the specific unit well using the pipettes 141 and 142 in a state in which the magnet mounting part 710 is lifted down and mixed with together to thereby separate impurities except for target protein from the magnetic particles.

Referring to FIGS. 5 and 8, a third magnetic field applying step S160 was provided. In the third magnetic field applying step S160, the lower portion of the specific unit well L inserted the unit well inserting groove by lifting up the magnet mounting part 710. Accordingly, a magnetic field was applied from the magnet 711 mounted on the magnet mounting part 710 to the lower portion of the specific unit well L.

Referring to FIGS. 5 and 8, a third removing step S170 was provided. The third removing step S170 was performed in a state in which a magnetic field is applied to the lower portion of the specific unit well L by the third magnetic field applying step S160. Therefore, in the third removing step S170, a state in which magnetic particles having the target proteins attached thereto in the mixture mixed with the washing solution were attached to an inner wall of the lower portion of the specific unit well L by a magnetic field was maintained.

In addition, in the third removing step S170, a mixture except for magnetic particles having the target proteins attached thereto in the mixture mixed with the washing solution was removed using the pipettes 141 and 142. The mixture removed from the third removing step S170 may be discharged to a unit well I of the multi well plate 420'. The third removing step S170 was performed, such that the magnetic particles having the target proteins attached thereto were left in the specific unit well L.

Washing step S150 separating impurities except for target protein from the magnetic particles by injecting a washing solution into the specific unit well and washing the magnetic particles, the third magnetic applying unit S160, and the third removing step S170 may be sequentially repeated several times and the mixture removed from the third step S170 is discharged to the waste tray 450.

Referring to FIGS. 5 and 8, a target protein separating step S180 purifying the target protein by injecting a protein eluting solution into the specific unit well was provided. In the target protein separating step S180, the protein eluting solution injected into the unit well E of the multi well plate 420 was injected into the specific unit well L using the pipettes 141 and 142 in a state in which the magnet mounting part 710 is lifted down and mixed with together to thereby separate the target protein from the magnetic particles.

Referring to FIGS. 5 and 8, a fourth magnetic field applying step S190 was provided. The fourth magnetic field applying step S190 was performed after the target protein separating step S180 purifying the target protein by injecting the protein eluting solution into the specific unit well and then a predetermined time is passed. In the fourth magnetic field applying step S190, the lower portion of the specific unit well L inserted the unit well inserting groove 713 by lifting up the magnet mounting part 710. Accordingly, a magnetic field was applied from the magnet mounted on the magnet mounting part 710 to the lower portion of the specific unit well L.

Referring to FIGS. 5 and 8, a target protein containing solution obtaining step S200 was provided. The target protein containing solution obtaining step S200 was performed in a state in which a magnetic field is applied to the lower portion of the specific unit well L by the fourth magnetic field applying step S190. Therefore, in the target protein containing solution obtaining step S200, a state in which the magnetic particles in the protein eluting solution containing the proteins separated from the magnetic particles were attached to an inner wall of the lower portion of the specific unit well L was maintained.

In the target protein containing solution obtaining step S200, the target protein containing solution which is a mixture except for the magnetic particles in the protein eluting solution containing the proteins separated from the magnetic particles was injected and stored into a protein storage tube 442-3 mounted on the base plate 400 using the pipettes 141 and 142.

(3) Experimental Results Using Protein Synthesis Kit

Results obtained by simultaneously synthesizing GFP in 16 reaction wells using the kit according to the present invention and ExiProgen™ (Bioneer Corporation, Korea) by Example 7 were shown in FIG. 11. More specifically, the results were confirmed in 10 to 12% SDS-PAGE gel, and it could be appreciated that a reproducible synthesis efficiency on the same proteins may be obtained due to no deviation between reaction wells.

In addition, results obtained by synthesizing each different protein using templates fabricated in various forms were shown in FIG. 12.

The invention claimed is:
1. A method of protein synthesis, the method comprising:
    (1) preparing a template for cell-free protein synthesis;
    (2) adding the template to a cell-free protein expression solution to express proteins;
    (3) adding magnetic particles coupled with an affinity tag to the expressed protein to attach a target protein to the magnetic particles; and
    (4) separating the attached target protein from the magnetic particles, wherein expression and purification of the target protein are simultaneously performed in an automatic system using an automatic biological material purification apparatus including: a heating part; and a magnetic field applying part,
    wherein the step (1) comprises:
    injecting step S10 injecting the template for cell-free protein synthesis into a unit well of the multi well plate kit 420'; and
    first mixing step S20 mixing a diethylpyrocarbonate distilled water injected into the unit well of the multi well plate kit 420' in order to dilute the template with the injected template,
    wherein the step (2) comprises:
    second mixing step S30 mixing the cell-free protein expression solution with the first mixture of the first mixing step;
    mixture preparing step S40 preparing a protein synthesis reaction solution by mixing the mixture of the second mixing step with a cell disrupted liquid; and
    heating step S50 applying heat to the protein synthesis reaction solution in the specific unit well by heating a lower portion of the specific unit well of the multi well plate kit 420' having the mixture using a heating part 720, wherein the step (3) comprises:

preparing step S70 of a magnetic particle reaction mixture;

protein expression injecting step S110 injecting the protein expression injected into the unit well of the multi well plate kit 420' into the prepared magnetic particle reaction mixture;

reacting step S120 reacting the protein expression injected into the unit well of the multi well plate kit 420' with the magnetic particle;

removing step S140 removing a mixture except for the magnetic particles and proteins coupled with the magnetic particle by applying a magnetic field to the mixture containing the protein expression;

washing step S150 washing impurities except for the target protein from the magnetic particle by injecting a washing solution injected into the unit well of the multi well plate kit 420; and removing step S170 removing a mixture except for the magnetic particles having the target proteins attached thereto from a washing solution containing mixture by applying a magnetic field to the washing solution containing mixture, and wherein the step (4) comprises:

target protein separating step S180 separating the target protein by injecting an eluting solution for the target protein injected into the unit well of the multi well plate kit 420 into a mixture obtained from the removing step; and target protein containing solution obtaining step S200 obtaining the target protein containing solution except for the magnetic particles from the eluting solution for the target protein containing the target protein separated from the magnetic particles by applying a magnetic field to the mixture.

2. The method of claim 1, wherein a second multi well plate kit 420' and a first multi well plate kit 420 are used, the second multi well plate kit 420' including:

(a) a solution for diluting the template for cell-free protein synthesis;

(b) the cell-free protein expression solution for expressing the target protein from the template; and the first multi well plate kit 420 including:

(c) a magnetic particle solution for attaching the target protein to the magnetic particles;

(d) the eluting solution for the target protein;

(e) a magnetic particle reaction solution for coupling the target protein with the magnetic particle and the washing solution.

3. The method of claim 1, wherein the template for cell-free protein synthesis is a deoxyribonucleic acid (DNA) having a circular form or a linear form.

4. The method of claim 3, wherein the DNA having a linear form is produced by obtaining a primary reactant by amplifying a target gene in a sample using a prepared primer set so as to amplify the target gene and provide overlapping sequences at 5' and 3' terminals; and secondarily amplifying the obtained primary reactant using a premix for PCR containing the following composition A, Composition A (a) an upstream cassette set and a downstream cassette set positioned at both 5' and 3' terminals of the target gene, and (b) a secondary primer set having overlapping sequences at both 5' and 3' terminals of the cassette set.

5. The method of claim 4, wherein the composition A contains 0.1 to 0.5 ng/ul of cassette set for encoding an affinity tag at both 5' and 3' terminals of the target gene and 0.1 to 1.0 pmoles/ul of each of secondary forward and reverse primers having overlapping sequences at 5' and 3' terminals of the cassette set.

6. The method of claim 4, wherein the affinity tag is histidine.

7. The method of claim 4, wherein the magnetic particle contains metal ions.

8. The method of claim 7, wherein the metal ion is a nickel ion.

9. The method of claim 1, wherein the washing step S150 washing impurities except for the target protein and the removing step S170 removing the mixture except for the magnetic particles having the target proteins attached thereto are sequentially performed once or more times.

10. The method of claim 1, wherein the target protein containing solution obtaining step S200 includes injecting the target protein containing solution into a protein storage tube 442-3.

11. The method of claim 1, wherein the magnetic particle is a magnetic particle coupled with a nickel ion.

* * * * *